(12) United States Patent
Doong et al.

(10) Patent No.: US 9,505,683 B2
(45) Date of Patent: Nov. 29, 2016

(54) REMOVAL OF SULFUR COMPOUNDS FROM NATURAL GAS STREAMS

(71) Applicant: UOP LLC, Des Plaines, IL (US)

(72) Inventors: Shain-Jer Doong, Kildeer, IL (US); Jayant K. Gorawara, Buffalo Grove, IL (US); Lubo Zhou, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 178 days.

(21) Appl. No.: 14/283,859

(22) Filed: May 21, 2014

(65) Prior Publication Data

US 2014/0357926 A1 Dec. 4, 2014

Related U.S. Application Data

(60) Provisional application No. 61/829,412, filed on May 31, 2013.

(51) Int. Cl.

| B01D 53/22 | (2006.01) |
|---|---|
| C07C 7/00 | (2006.01) |
| C10L 3/10 | (2006.01) |
| B01D 53/04 | (2006.01) |
| B01D 53/14 | (2006.01) |
| B01D 53/26 | (2006.01) |

(52) U.S. Cl.
CPC ............... *C07C 7/005* (2013.01); *B01D 53/04* (2013.01); *B01D 53/1462* (2013.01); *B01D 53/261* (2013.01); *C10L 3/10* (2013.01); *C10L 3/103* (2013.01); *C10L 3/104* (2013.01); *C10L 3/106* (2013.01); *B01D 2252/204* (2013.01); *B01D 2253/108* (2013.01); *B01D 2253/1124* (2013.01); *B01D 2256/245* (2013.01); *B01D 2257/304* (2013.01); *B01D 2257/306* (2013.01); *B01D 2257/308* (2013.01); *B01D 2257/504* (2013.01); *B01D 2257/602* (2013.01); *B01D 2257/80* (2013.01); *C10L 2290/08* (2013.01); *C10L 2290/12* (2013.01); *C10L 2290/541* (2013.01); *C10L 2290/542* (2013.01); *Y02C 10/06* (2013.01); *Y02C 10/08* (2013.01)

(58) Field of Classification Search
CPC .... B01D 53/22; B01D 53/02; B01D 53/005; B01D 53/14; B01D 53/1406; B01D 53/46; C07C 7/005; C07C 7/11; C07C 7/12; C07C 7/13; C07C 7/144; C10G 25/05; C10G 25/12
USPC ............... 95/51, 45, 49, 90, 114; 585/800 S
See application file for complete search history.

(56) References Cited

U.S. PATENT DOCUMENTS

| 8,282,707 B2 * | 10/2012 | Bresler | ............... | B01D 53/75 95/114 |
| 2012/0000359 A1 * | 1/2012 | Bresler | ............... | B01D 53/75 95/51 |

\* cited by examiner

*Primary Examiner* — Sharon Pregler

(57) ABSTRACT

A process for treatment of a natural gas stream, or other methane containing stream that passes through a guard bed for removal of mercury and hydrolysis of COS, followed by treatment with an absorbent unit containing an amine solvent for removal of carbon dioxide and hydrogen sulfide. The gas is then dried by a molecular sieve bed. The regeneration gas for the molecular sieve adsorbent bed is chilled to remove liquid hydrocarbons and sulfur compounds. The process is accomplished without the use of an absorbent unit to remove the sulfur compounds.

7 Claims, 3 Drawing Sheets

REMOVAL OF SULFUR COMPOUNDS FROM NATURAL GAS STREAMS

CROSS-REFERENCE TO RELATED APPLICATION

This application claims priority from Provisional Application No. 61/829,412 filed May 31, 2013, the contents of which are hereby incorporated by reference.

BACKGROUND OF THE INVENTION

Natural gas processing can range from simple treating and conditioning for pipeline delivery to complex operations needed to meet specifications to produce pipeline sales gas or liquefied natural gas (LNG). Removal of acid gas compounds such as carbon dioxide and hydrogen sulfide as well as removal of organic sulfur compounds, water and mercury is required to meet end product specifications and to avoid product blockages in downstream process equipment. The level of treatment that is required varies according to the treated gas product specifications as well as local environmental regulations.

In some prior art treatment facilities, mercury is removed by a non-regenerable guard bed and carbon dioxide and hydrogen sulfide are removed by a solvent process employing a solvent such as an amine. Water may be removed by a molecular sieve dehydration unit. The more difficult challenge is to remove COS and organic sulfur compounds such as mercaptans, disulfides, and polysulfides. Historically, there are two types of flow schemes to remove these organic sulfur compounds to meet the product requirements. One is a gas-phase treatment, where the molecular sieve unit is designed to remove the organic sulfur compounds into its regeneration gas stream. The regeneration gas is then treated by a physical solvent unit such as a Selexol™ process to produce a sale or fuel gas and an acid gas stream containing the organic sulfur compounds. This acid gas stream, along with the acid gas generated in the amine unit, is then sent to a sulfur plant such as one operating a Claus process for sulfur recovery. The other flow scheme that has been used is a liquid phase treatment, where all or most of the carbonyl sulfide, organic sulfur compounds or both, are allowed to pass through the dehydration unit. If a natural gas liquid (NGL) unit exists, sulfur compounds are expected to be concentrated in the NGL stream. The NGL liquids or an after fractionation stream are then specialty-amine treated specifically for COS removal. Mercaptans are removed by a regenerable caustic process such as a Merox process in which the mercaptans are converted to liquid hydrocarbon disulfides through use of caustics such as sodium hydroxide or ammonia. Finally, the liquid is sulfur-polished to a low sulfur concentration by a molecular sieve unit to remove the remaining sulfur content.

The gas phase treatment option requires the expense of a sulfur plant while the liquid phase option requires an NGL unit. The liquid phase scheme also has an unattractive element in the caustic-based treatment and its associated spent caustic disposal problem. A sulfur plant is quite costly and it is only justified when the sulfur level is high. The use of an NGL plant is only justified when the gas is rich in $C_2$, $C_3$ and $C_4$ components. If the gas processing operator receives the feed gas from different supply sources, the feed gas sulfur level and/or its hydrocarbon contents may vary from time to time, which would not mean that neither a sulfur plant nor an NGL unit would be justified. Due to the shortcomings of the existing systems, an alternative sulfur capture technology is needed. An ideal solution would be to turn these sulfur compounds into either a solid or a liquid form so that they could be physically transported out of the gas processing facility.

SUMMARY OF THE INVENTION

The invention follows a gas-phase treatment route with a physical solvent unit being replaced by a chilling unit to condense the organic sulfur compounds. In an embodiment of the invention, the gas is first treated by a mercury adsorbent guard bed to remove mercury and mercury compounds. The mercury adsorbent may be a metal oxide-based material, such as a copper oxide material, supported in an alumina substrate. The presence of alumina, promotes carbonyl sulfide in the feed gas to be hydrolyzed to hydrogen sulfide. The gas may then enter an amine unit to remove carbon dioxide to less than a 50 ppm-vol level and hydrogen sulfide removed to less than 1 ppm-vol. Additional COS removal in the amine unit may also take place depending upon selection of the appropriate amine solvent. The water-saturated gas may be fed to a molecular sieve unit to remove water and all organic sulfur compounds. The treated gas, which is dry and nearly sulfur-free, is then sent to the down-stream processing unit, NGL or LNG train or to the gas pipeline.

An embodiment of the invention involves a process for treating a natural gas stream comprising removing mercury in an adsorbent guard bed that may contain a metal oxide adsorbent such as copper oxide, removing carbon dioxide and hydrogen sulfide in a solvent absorbent unit, then removing water and organic sulfur compounds in a second adsorbent bed, then regenerating the second adsorbent bed with a heated gas stream to remove water and sulfur compounds.

In this process, carbonyl sulfide within the natural gas stream is hydrolyzed in the adsorbent guard bed to hydrogen sulfide and a portion of the carbonyl sulfide may be removed in the second adsorbent bed. Each adsorbent bed will consist of one or more adsorbent beds, such as a set of three, five or more beds. The heated gas stream contains water and sulfur and is first cooled to remove water, then dried to remove additional water and then cooled to a sufficient temperature to condense organic sulfur compounds for removal.

The heated gas exits the second adsorbent bed and then it is cooled to remove water and to produce a cooled gas stream. Liquid hydrocarbons as well as sulfur compounds are removed from the cooled gas stream.

DETAILED DESCRIPTION OF THE INVENTION

Figure 1:
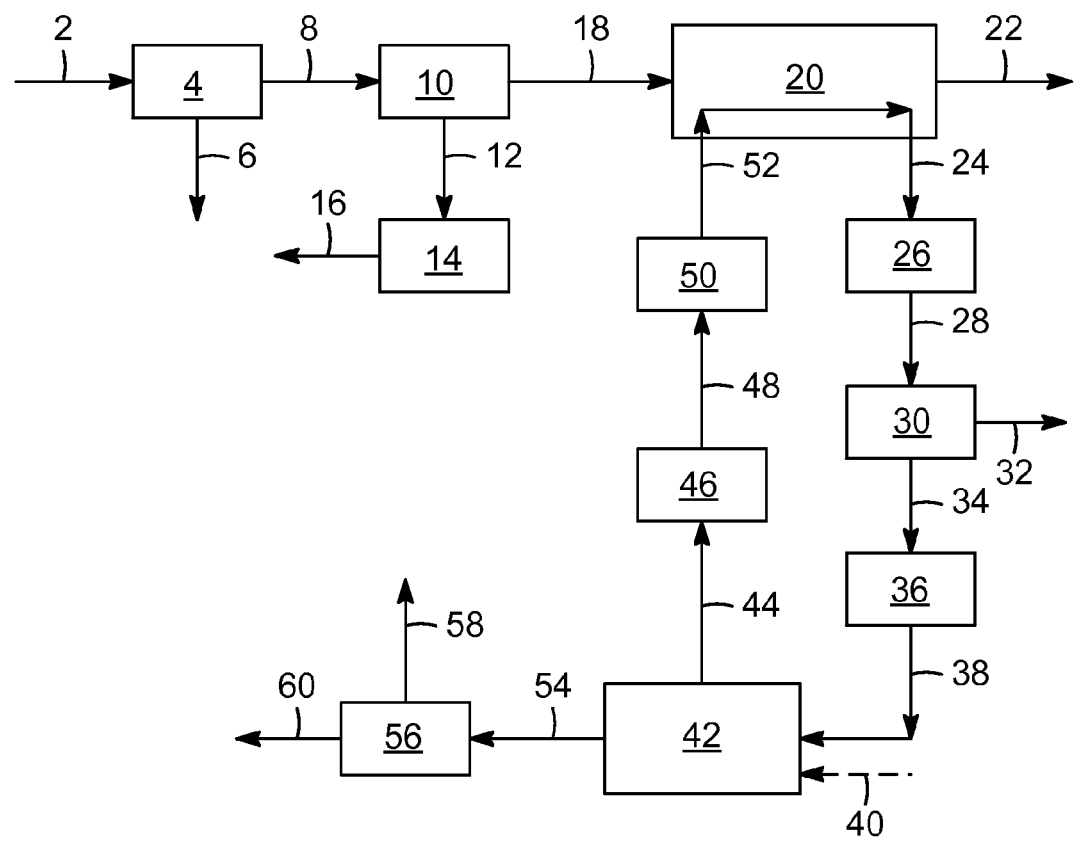
FIG. 1 shows an embodiment of the invention for treating a natural gas stream and separately recovering natural gas liquids and sulfur compounds.
Figure 2:
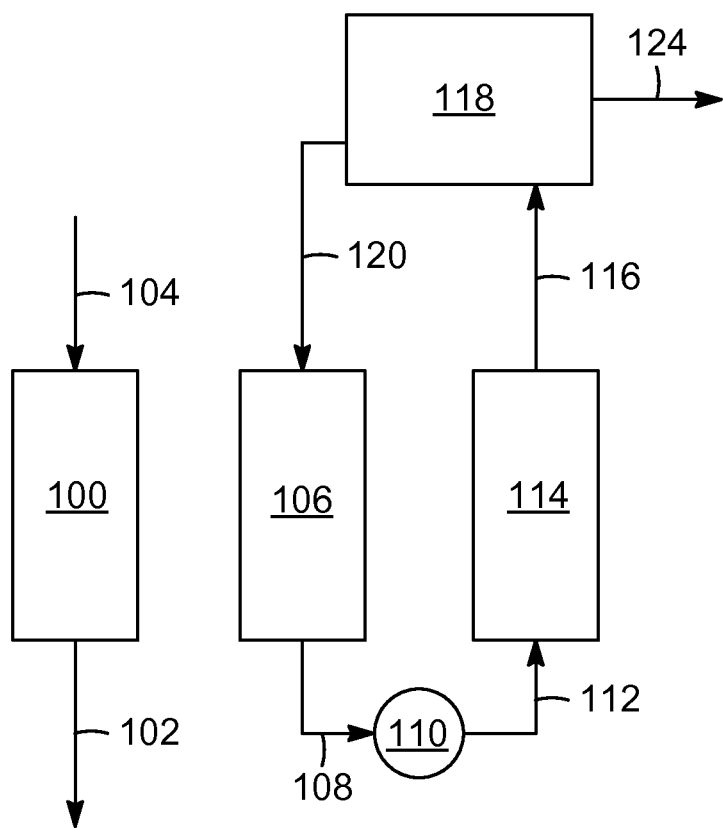
FIG. 2 shows a closed loop adsorbent bed regeneration configuration.

The adsorbent regeneration gas, which contains all removed sulfur compounds and water, is first cooled to knock out water. It is then further dried in a small MolSiv unit to remove water down to ppm-wt level. This is followed by a chiller to cool the gas temperature sufficiently to condense the organic sulfur compounds which are separated from a gas-liquid separator. The gas is returned to the molecular sieve unit, after boosting its pressure by a blower, for the purpose of bed regeneration. FIG. 2 shows the concept of this closed-loop MolSiv regeneration gas scheme, using a 3-bed temperature swing adsorption in this example, although larger systems may also be used. Essentially, the returned regeneration gas is first used to cool one of the adsorber beds (Bed B in FIG. 2). As the gas enters the adsorber concurrently or from the feed end, this cooling gas does not need to be sulfur-free. The outlet of the adsorber, which is nearly sulfur-free is heated and sent to bed C for hot regeneration. The outlet of the bed C is then cooled, dehydrated, and further chilled to remove sulfur compounds as shown in FIG. 1 or depicted as a treatment box in FIG. 2.

The liquid collected from the gas-liquid separator is sent to a distillation column to stabilize the liquid. The liquid can be trucked off-site to a nearby refinery in its hydro processing unit. The small amount of the residue gas can be recycled back to the amine unit after recompression. The acid gas from the amine unit, which contains mostly $H_2S$ and COS can be adsorbed by a non-regenerable guard bed adsorbent. The spent adsorbent can be disposed of as a solid waste or sent to a third party for reclaiming the metal content of the adsorbent.

Optionally, a liquid hydrocarbon stream, either available from the plant condensate or downstream NGL unit, can be injected to the regeneration gas stream before the chiller to facilitate the condensation of the sulfur compounds. Furthermore, an absorber column using the liquid hydrocarbon can be used to facilitate the separation of the heavy sulfur compounds from the light hydrocarbon gas.

One of the major benefits using the above closed-loop regeneration scheme for the adsorbent unit as shown in FIG. 2 is for handling the high oxygen contents in the natural gas feed stream. Oxygen can react with sulfur compounds to form elemental sulfur during the hot regeneration step of the adsorbent unit. The typical limit of the oxygen concentration is about 10 ppm-vol. In a closed loop regeneration mode, if the regeneration gas is made nearly oxygen-free, additional oxygen brought by the feed stream will not enter the regeneration loop except under these two conditions. In some cases, make-up regeneration gas is needed. In this case, a small de-oxygen reactor can be installed in the make-up stream from the adsorbent product gas, which is sulfur-free and would not affect the catalyst (typically precious metal) of the de-oxygen reactor. On other occasions, oxygen is present in the void space of the adsorbent at the end of the feed step or before the hot regeneration. In this case, a purge step can be added before the gas temperature is raised to the regeneration temperature.

The regeneration gas can be made nearly oxygen-free after a number of cycles from the start-up, as oxygen will be gradually consumed at a high temperature during these initial cycles.

The invention is shown in the FIGURES. In FIG. 1, a natural gas feed 2 is sent to adsorbent guard bed 4 with mercury removal shown being removed in line 6. Carbonyl sulfide is hydrolyzed to form hydrogen sulfide which is more easily removed. The gas feed then is sent through line 8 to absorber unit 10 which may use an amine solvent or other appropriate solvent to remove carbon dioxide and hydrogen sulfide shown in line 12, and then being sent to guard bed 14 and then on to disposal of the adsorbent shown in line 16. The purified gas stream from absorber unit 10 then is sent through line 18 to one or more adsorbent beds 20 for removal of water and other impurities. The treated gas is shown being removed in line 22 and then can be further treated or transported as appropriate. Below adsorbent beds 20 is shown the system for removal of the liquid hydrocarbons and for regenerating the adsorbent in adsorbent beds 20. A gas 44 is sent from gas/liquid separator 42 to blower 46, then through line 48 to a heater 50 and then through line 52 to adsorbent bed 20. This heated gas removes water and other liquids such as liquid hydrocarbons and then circulates to line 24, then to a cooler 26. The cooled gas is sent through line 28 to a dehydrator 30 to remove water in line 32 and the remaining gas then is sent through line 34 to chiller 36 and then to gas/liquid separator 42. A liquid stream containing liquid hydrocarbon is sent from gas/liquid separator 42 through line 54 to a stabilizer unit 56 for further processing with a small gas portion 58 recycled to guard bed 4 or absorber 10 for further processing. The liquid hydrocarbons are sent through line 60 to be sent to a distillation column (not shown) and it can be sent to a refinery.

FIG. 2 shows the use of a closed loop regeneration gas scheme for a 3 bed temperature swing adsorption group (corresponding to adsorbent bed 20 in FIG. 1). A returned regeneration gas 120 is used to cool adsorbent bed 106 and then passes through line 108 to heater 110 to line 112 and then to adsorbent bed 114. The gas then goes through line 116 to a treatment box 118 with water and sulfur compounds exiting in line 124.

Figure 3:
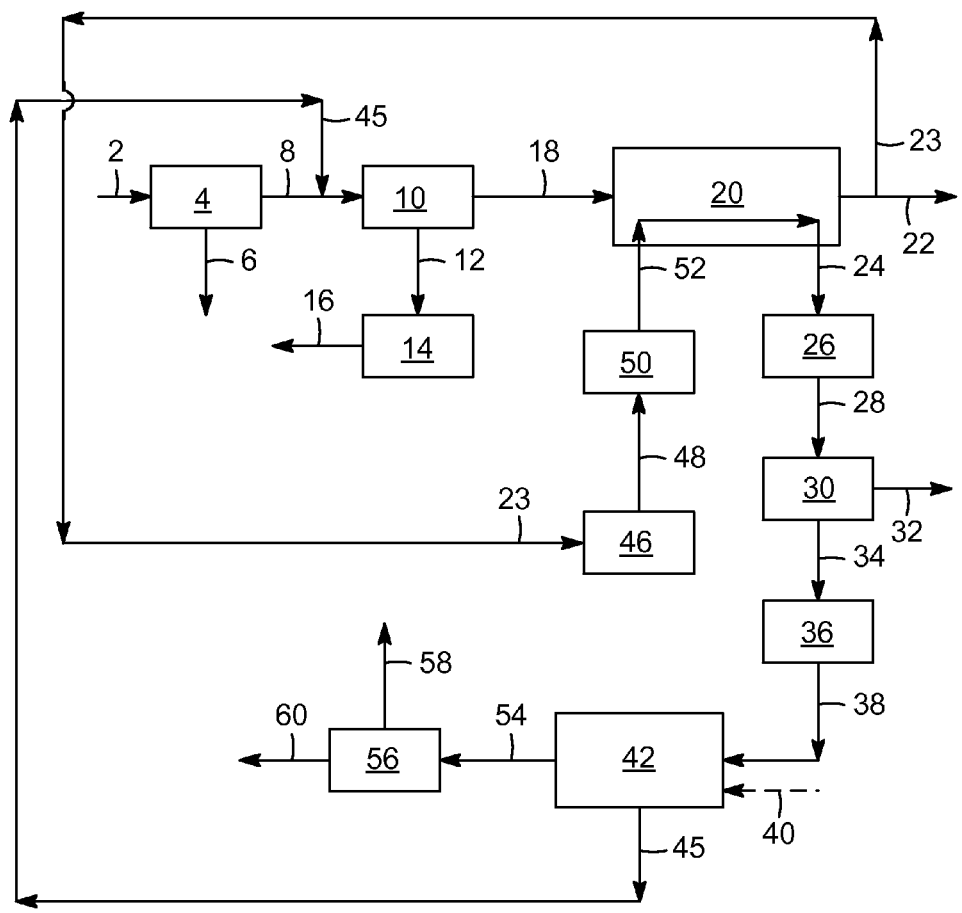
FIG. 3 shows an alternate embodiment of the invention showing a treated product slipstream regenerating the adsorbent beds.

FIG. 3 shows a natural gas feed 2 is sent to adsorbent guard bed 4 with mercury removal shown being removed in line 6. Carbonyl sulfide is hydrolyzed to form hydrogen sulfide which is more easily removed. The gas feed then is sent through line 8 to absorber unit 10 which may use an amine solvent or other appropriate solvent to remove carbon dioxide and hydrogen sulfide shown in line 12, and then being sent to guard bed 14 and then on to disposal of the adsorbent shown in line 16. The purified gas stream from absorber unit 10 then is sent through line 18 to one or more adsorbent beds 20 for removal of water and other impurities. The treated gas is shown being removed in line 22 and then can be further treated or transported as appropriate. Below adsorbent beds 20 is shown the system for removal of the liquid hydrocarbons and for regenerating the adsorbent in adsorbent beds 20. Also shown, is a slipstream 23 removed from the treated gas in line 22. This slipstream 23 is then shown inserted at blower 46 then through line 48 to a heater 50 and then through line 52 to adsorbent bed 20. This heated gas removes water and other liquids such as liquid hydrocarbons and then circulates to line 24, then to a cooler 26. The cooled gas is sent through line 28 to a dehydrator 30 to remove water in line 32 and the remaining gas then is sent through line 34 to chiller 36 and then to gas/liquid separator 42. A liquid stream containing liquid hydrocarbon is sent from gas/liquid separator 42 through line 54 to a stabilizer unit 56 for further processing with a small gas portion 58 recycled to guard bed 4 or absorber 10 for further processing. The liquid hydrocarbons are sent through line 60 to be sent to a distillation column (not shown) and it can be sent to a refinery. A gas stream 45 is sent from gas/liquid separator 42 to be combined with the gas being sent to absorber unit 10.

The present invention may provide one or more of the following benefits. A first adsorbent bed 100 is shown in operation, treating feed 104 and producing purified feed 102. A returned regeneration gas 120 is used to cool adsorbent bed 106 process may be operated without a Sulfur plant or NGL unit. All sulfur species are either converted to liquid form or sequestered in a solid adsorbent. As such, they can be easily transported. No caustic treatment is required for an NGL liquid. MolSiv S-polishing can be used for NGL if needed. The process may be operated without the use of a physical solvent process. There is a minimum or even no hydrocarbon loss which is particularly beneficial if the liquid is to be sold to a refinery. The process includes a mercury guard bed, amine, adsorbent bed and propane chilling.

The following example demonstrates an embodiment of the current invention.

A natural gas stream at a flow rate of 692 MMSCFD at 43 bar and 45° C. with a composition shown in the Table is to be purified by removal of its water, carbon dioxide and sulfur contents before sending into an LNG train. Using the process flow scheme from the current invention as shown in FIGS. 1 and 2, mercury is removed by a copper-based adsorbent. COS is also partially converted to $H_2S$ in the same guard bed. COS is further removed by the amine unit down to about 2 ppm-vol. Carbon dioxide is removed to below 50 ppm-vol and $H_2S$ to 1 ppm-vol by the amine unit.

A 5-bed adsorbent unit packed with 5A and 13 X molecular sieves is used to remove water and all remaining sulfur compounds. The treated product gas compositions are shown in the third column of the Table. The regeneration gas is first cooled by an air cooler to about 45° C. to knock out liquid water. The regeneration gas is dried by a 2-bed adsorbent unit packed with 3 A zeolite molecular sieve. A propane chiller is used to further cool the gas to about minus 30° C. to condense sulfur compounds. The cold liquid is stabilized to a final composition as shown in the Table. About 9464 liters (2500 gallons) per day of liquid are produced.

TABLE

|  | feed | product | liquid |
|---|---|---|---|
| NITROGEN | 5.07E−03 | 5.11E−03 | 1.38E−09 |
| CARBON DIOXIDE | 6.86E−03 | 4.88E−05 | 8.59E−05 |
| METHANE | 0.969305 | 0.97683 | 3.10E−02 |
| ETHANE | 1.41E−02 | 1.43E−02 | 2.07E−02 |
| PROPANE | 2.47E−03 | 2.46E−03 | 1.70E−02 |
| ISOBUTANE | 4.90E−04 | 4.68E−04 | 7.72E−03 |
| n-BUTANE | 5.70E−04 | 5.43E−04 | 0.01553 |
| n-PENTANE | 2.10E−04 | 1.67E−04 | 1.64E−02 |
| ISOPENTANE | 1.50E−04 | 1.20E−04 | 8.59E−03 |
| n-HEXANE | 4.00E−04 | 0 | 6.32E−02 |
| BENZENE | 1.60E−05 | 0 | 3.86E−03 |
| WATER | 1.20E−04 | 0 | 0.00E+00 |
| HYDROGEN SULFIDE | 5.22E−06 | 8.82E−09 | 3.02E−04 |
| CARBONYL SULFIDE | 6.12E−05 | 1.80E−06 | 1.70E−05 |
| METHYL MERCAPTAN | 1.88E−05 | 0 | 0.143591 |
| ETHYL MERCAPTAN | 6.65E−06 | 0 | 5.16E−02 |
| n-PROPYL MERCAPTAN | 5.50E−06 | 0 | 0.042709 |
| PHENYL MERCAPTAN | 2.83E−05 | 0 | 0.201645 |
| DIMETHYL SULFIDE | 3.23E−06 | 0 | 2.51E−02 |
| CARBON DISULFIDE | 5.29E−06 | 0 | 4.09E−02 |
| METHYL ETHYL SULFIDE | 1.54E−06 | 0 | 1.20E−02 |
| DIMETHYL DISULFIDE | 2.09E−06 | 0 | 1.61E−02 |
| ETHYL METHYL DISULFIDE | 3.08E−06 | 0 | 2.33E−02 |
| DIETHYL DISULFIDE | 1.54E−06 | 0 | 0.011331 |
| BENZOTHIOPHENE | 4.67E−05 | 0 | 0.221985 |
| 2-METHYL BENZOTHIOPHENE | 1.08E−05 | 0 | 2.55E−02 |

Specific Embodiments

While the following is described in conjunction with specific embodiments, it will be understood that this description is intended to illustrate and not limit the scope of the preceding description and the appended claims.

A first embodiment of the invention is a process for treating a natural gas stream comprising removing mercury in an adsorbent guard bed, removing carbon dioxide and hydrogen sulfide in a solvent absorbent unit, then removing water and organic sulfur compounds in a second adsorbent bed, then regenerating the second adsorbent bed with a heated gas stream to remove water and sulfur compounds. An embodiment of the invention is one, any or all of prior embodiments in this paragraph up through the first embodiment in this paragraph wherein carbonyl sulfide within the natural gas stream is hydrolyzed in the adsorbent guard bed to hydrogen sulfide. An embodiment of the invention is one, any or all of prior embodiments in this paragraph up through the first embodiment in this paragraph wherein the heated gas stream contains water and sulfur and is first cooled to remove water, then dried to remove additional water and then cooled to a sufficient temperature to condense organic sulfur compounds for removal. An embodiment of the invention is one, any or all of prior embodiments in this paragraph up through the first embodiment in this paragraph wherein the adsorbent guard bed comprises a metal oxide adsorbent. An embodiment of the invention is one, any or all of prior embodiments in this paragraph up through the first embodiment in this paragraph wherein a majority of carbonyl sulfide within the natural gas stream is hydrolyzed in the adsorbent guard bed to hydrogen sulfide and a portion of the carbonyl sulfide is removed in the second adsorbent bed. An embodiment of the invention is one, any or all of prior embodiments in this paragraph up through the first embodiment in this paragraph wherein the heated gas exits the second adsorbent bed and then the heated gas is cooled to remove water and to produce a cooled gas stream. An embodiment of the invention is one, any or all of prior embodiments in this paragraph up through the first embodiment in this paragraph wherein liquid hydrocarbons are removed from the cooled gas stream. An embodiment of the invention is one, any or all of prior embodiments in this paragraph up through the first embodiment in this paragraph wherein sulfur compounds are removed from the cooled gas stream. An embodiment of the invention is one, any or all of prior embodiments in this paragraph up through the first embodiment in this paragraph wherein the sulfur compounds are organic sulfur compounds.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for treating a natural gas stream comprising:
   a) sending said natural gas stream to an adsorbent guard bed to remove mercury to produce a first stream;
   b) sending the first stream to a solvent absorbent bed unit to remove carbon dioxide and hydrogen sulfide to produce a second stream;
   c) sending the second stream to a second adsorbent bed to remove water and organic sulfur compounds to produce a third stream;

d) wherein after said second stream has passed to said second adsorbent bed, regenerating the second adsorbent bed with a heated gas stream comprising said third stream to remove water and sulfur from the second adsorbent bed, then cooling and drying said second adsorbent bed to further remove water and organic sulfur compounds.

2. The process of claim 1 wherein said organic sulfur compounds comprise carbonyl sulfide and within said natural gas stream said carbonyl sulfide is hydrolyzed in said adsorbent guard bed to hydrogen sulfide.

3. The process of claim 1 wherein said adsorbent guard bed comprises a metal oxide adsorbent.

4. The process of claim 2 wherein a majority of said carbonyl sulfide within said natural gas stream is hydrolyzed in said adsorbent guard bed to hydrogen sulfide and a portion of said carbonyl sulfide is removed in said second adsorbent bed.

5. The process of claim 1 wherein said heated gas exits said second adsorbent bed and then said heated gas is cooled to remove water and to produce a cooled gas stream.

6. The process of claim 5 wherein liquid hydrocarbons that were in said natural gas stream are removed from said cooled gas stream.

7. The process of claim 6 wherein organic sulfur compounds and hydrogen sulfide are removed from said cooled gas stream.

\* \* \* \* \*